(12) United States Patent
Le et al.

(10) Patent No.: US 9,974,928 B2
(45) Date of Patent: May 22, 2018

(54) APPARATUS FOR SECURING A MEDICAL CLAMP TO A PATIENT

(75) Inventors: Minhhia Ngan Le, Shrewsbury, MA (US); Duc Hong Le, Shrewsbury, MA (US)

(73) Assignee: SafeSharp Technologies Corporation, Shrewsbury, MA (US)

( * ) Notice: Subject to any disclaimer, the term of this patent is extended or adjusted under 35 U.S.C. 154(b) by 190 days.

(21) Appl. No.: 14/116,168

(22) PCT Filed: May 9, 2012

(86) PCT No.: PCT/US2012/037032
§ 371 (c)(1),
(2), (4) Date: Jan. 15, 2014

(87) PCT Pub. No.: WO2012/154791
PCT Pub. Date: Nov. 15, 2012

(65) Prior Publication Data
US 2014/0148789 A1 May 29, 2014

Related U.S. Application Data

(60) Provisional application No. 61/518,680, filed on May 10, 2011.

(51) Int. Cl.
*A61M 25/02* (2006.01)
*A61B 17/068* (2006.01)
*A61B 17/064* (2006.01)

(52) U.S. Cl.
CPC ......... *A61M 25/02* (2013.01); *A61B 17/0682* (2013.01); *A61B 17/0644* (2013.01);
(Continued)

(58) Field of Classification Search
CPC .............. A61B 17/068; A61B 17/0684; A61B 17/07207; A61B 17/115; A61B 17/1152;
(Continued)

(56) References Cited

U.S. PATENT DOCUMENTS 3,068,889 A    12/1962   Swenson
4,164,943 A    8/1979   Hill et al.
(Continued)

FOREIGN PATENT DOCUMENTS

ES           2336354 T3    4/2010
WO   WO 93/16751 A1   9/1993

OTHER PUBLICATIONS

International Search Report and Written Opinion for Application No. PCT/US2012/037032 dated Aug. 16, 2012.
(Continued)

*Primary Examiner* — Christopher L Templeton
(74) *Attorney, Agent, or Firm* — Wolf, Greenfield & Sacks, P.C.

(57) ABSTRACT

Methods and apparatus for actuating first and second fasteners to secure a medical clamp to a patient. An exemplary fastening device comprises a first rotatable member configured to rotate from an outward position to an inward position to engage the first fastener and a second rotatable member configured to rotate from an outward position to an inward position to engage the second fastener. The first and second rotatable members are mechanically coupled to enable concurrent engagement of the first and second fasteners.

12 Claims, 17 Drawing Sheets

(52) U.S. Cl.
CPC .... *A61B 17/0684* (2013.01); *A61M 2025/024* (2013.01); *A61M 2025/028* (2013.01); *A61M 2025/0286* (2013.01)

(58) Field of Classification Search
CPC .............. A61B 17/0682; A61B 17/072; A61B 2017/07228; A61B 2017/07257; A61B 2017/1157; A61B 17/0686; A61B 17/128; A61B 17/1285; A61B 17/10; A61B 2017/2933; A61B 2017/07214; A61B 2017/301; A61B 2017/2906; A61B 2017/2919; A61B 2017/2926; A61B 2017/2944; A61B 2017/2932; A61B 17/29

See application file for complete search history.

(56) References Cited

U.S. PATENT DOCUMENTS

| | | | | |
|---|---|---|---|---|
| 4,821,939 | A * | 4/1989 | Green | A61B 17/072 227/19 |
| 4,930,674 | A * | 6/1990 | Barak | A61B 17/072 227/179.1 |
| 5,304,183 | A * | 4/1994 | Gourlay | A61B 17/00234 227/901 |
| 5,425,489 | A * | 6/1995 | Shichman | A61B 17/0643 227/108 |
| 5,490,856 | A * | 2/1996 | Person | A61B 17/072 227/175.1 |
| 5,520,664 | A | 5/1996 | Bricault, Jr. et al. | |
| 5,540,648 | A | 7/1996 | Yoon | |
| 5,618,311 | A * | 4/1997 | Gryskiewicz | A61B 17/064 606/216 |
| 5,620,452 | A * | 4/1997 | Yoon | A61B 17/0643 606/151 |
| 5,833,695 | A * | 11/1998 | Yoon | A61B 17/072 227/176.1 |
| 6,139,563 | A * | 10/2000 | Cosgrove, III | A61B 17/122 600/564 |
| 6,248,117 | B1 | 6/2001 | Blatter | |
| 6,544,271 | B1 * | 4/2003 | Adams | A61B 17/07207 606/139 |
| 6,572,587 | B2 | 6/2003 | Lerman et al. | |
| 7,794,471 | B1 * | 9/2010 | Bender | A61B 17/11 606/142 |
| 2001/0056261 | A1 | 12/2001 | Lerman et al. | |
| 2003/0014064 | A1 * | 1/2003 | Blatter | A61B 17/0644 606/153 |
| 2003/0045890 | A1 * | 3/2003 | Crainich | A61B 17/0682 606/139 |
| 2003/0078596 | A1 * | 4/2003 | Banbury | A61B 17/0644 606/131 |
| 2004/0215217 | A1 * | 10/2004 | Banbury | A61B 17/0644 606/151 |
| 2004/0249391 | A1 | 12/2004 | Cummins | |
| 2005/0049618 | A1 * | 3/2005 | Masuda | A61B 17/122 606/151 |
| 2005/0075657 | A1 * | 4/2005 | Bombard | A61B 17/1152 606/153 |
| 2005/0107807 | A1 * | 5/2005 | Nakao | A61B 17/1222 606/139 |
| 2005/0149064 | A1 * | 7/2005 | Peterson | A61B 17/064 606/143 |
| 2005/0274768 | A1 * | 12/2005 | Cummins | A61B 17/0057 227/175.1 |
| 2005/0283119 | A1 | 12/2005 | Uth et al. | |
| 2006/0122635 | A1 * | 6/2006 | Naegeli | A61B 17/068 606/142 |
| 2006/0135988 | A1 * | 6/2006 | Peterson | A61B 17/04 606/210 |
| 2006/0151568 | A1 | 7/2006 | Weller et al. | |
| 2006/0190035 | A1 * | 8/2006 | Hushka | A61B 17/2909 606/205 |
| 2007/0213585 | A1 * | 9/2007 | Monassevitch | A61B 17/0643 600/104 |
| 2009/0054843 | A1 | 2/2009 | Lundqvist | |
| 2009/0054916 | A1 * | 2/2009 | Meier | A61B 17/122 606/158 |
| 2009/0206127 | A1 * | 8/2009 | Danielson | A61B 17/064 227/175.1 |
| 2010/0042140 | A1 * | 2/2010 | Cunningham | A61B 17/29 606/205 |
| 2010/0217314 | A1 | 8/2010 | Holsten et al. | |
| 2012/0116427 | A1 | 5/2012 | Raza | |
| 2012/0209217 | A1 | 8/2012 | Gray | |
| 2015/0005733 | A1 | 1/2015 | Le et al. | |

OTHER PUBLICATIONS

International Preliminary Report on Patentability for Application No. PCT/US2014/037032 dated Nov. 21, 2013.
International Search Report and Written Opinion for Application No. PCT/US2014/044742 dated Dec. 23, 2014.
International Preliminary Report on Patentability for Application No. PCT/US2014/044742 dated Jan. 7, 2016.
Extended European Search Report for Application No. EP 14818572.1 dated Jan. 11, 2017.

* cited by examiner

APPARATUS FOR SECURING A MEDICAL CLAMP TO A PATIENT

CROSS-REFERENCE TO RELATED APPLICATIONS

This application claims a priority benefit, under 35 U.S.C. § 119(e), to U.S. provisional patent application Ser. No. 61/518,680, entitled "Medical Clamp Fastener System and Surgical Stapler for Same," filed on May 10, 2011. This application is incorporated herein by reference.

FIELD

This application relates to an improved medical clamp fastener system and a surgical stapler for same.

BACKGROUND

A central venous catheter is a catheter typically placed into a large vein in the neck, chest or groin. The catheter may be used to administer medication or fluids, obtain blood tests, obtain cardiovascular measurements, and the like.

A catheter clamp system may be used to secure the catheter in place on the patient. One conventional catheter clamp system includes a sleeve about the catheter. A clamp with apertures for receiving sutures is then attached to the sleeve. The clamp is then stitched through the apertures and into the skin of a patient to secure the clamp in place on the patient.

However, stitching a conventional catheter clamp system to the skin of a patient takes time and is more prone to accidental needle stick injuries to the medical professional and/or transmission of infection from the patient to the medical professional as a result of such needle stick injuries.

One conventional medical device anchoring system for securing a catheter to a patient is disclosed in U.S. Pat. No. 7,799,000. As disclosed therein, a fixation apparatus includes opposing wings that include a staple receiving portion allegedly configured to receive surgical staples. The stapling receiving portions each have distal and proximate ends that include staple retaining ends that are configured to inhibit the staple receiving portions from dislodging from staples. The fixation apparatus also includes apertures 27 used for conventional sutures.

SUMMARY

One embodiment described herein is directed to a fastening device for actuating first and second fasteners to secure a medical clamp to a patient. The fastening device comprises a first rotatable member configured to rotate from an outward position to an inward position to engage the first fastener and a second rotatable member configured to rotate from an outward position to an inward position to engage the second fastener. The first and second rotatable members are mechanically coupled to enable concurrent engagement of the first and second fasteners.

Another embodiment described herein is directed to an apparatus for securing a medical device to a patient. The apparatus comprises a medical clamp and a fastening device for the actuating first and second fasteners to secure the medical clamp to a patient. The fastening device comprises a first rotatable member configured to rotate from an outward position to an inward position to engage the first fastener and a second rotatable member configured to rotate from an outward position to an inward position to engage the second fastener. The first and second rotatable members are mechanically coupled to enable concurrent engagement of the first and second fasteners.

A further embodiment described herein is directed to a method of actuating first and second fasteners to secure a medical clamp to a patient. The method comprises rotating a first rotatable member of a fastening device from an outward position to an inward position to engage the first fastener and, concurrent with rotating the first rotatable member, rotating a second rotatable member of the fastening device from an outward position to an inward position to engage the second fastener.

BRIEF DESCRIPTION OF THE DRAWINGS

Other objects, features and advantages will occur to those skilled in the art from the following description of a preferred embodiment and the accompanying drawings, in which.

DETAILED DESCRIPTION

Figure 1:
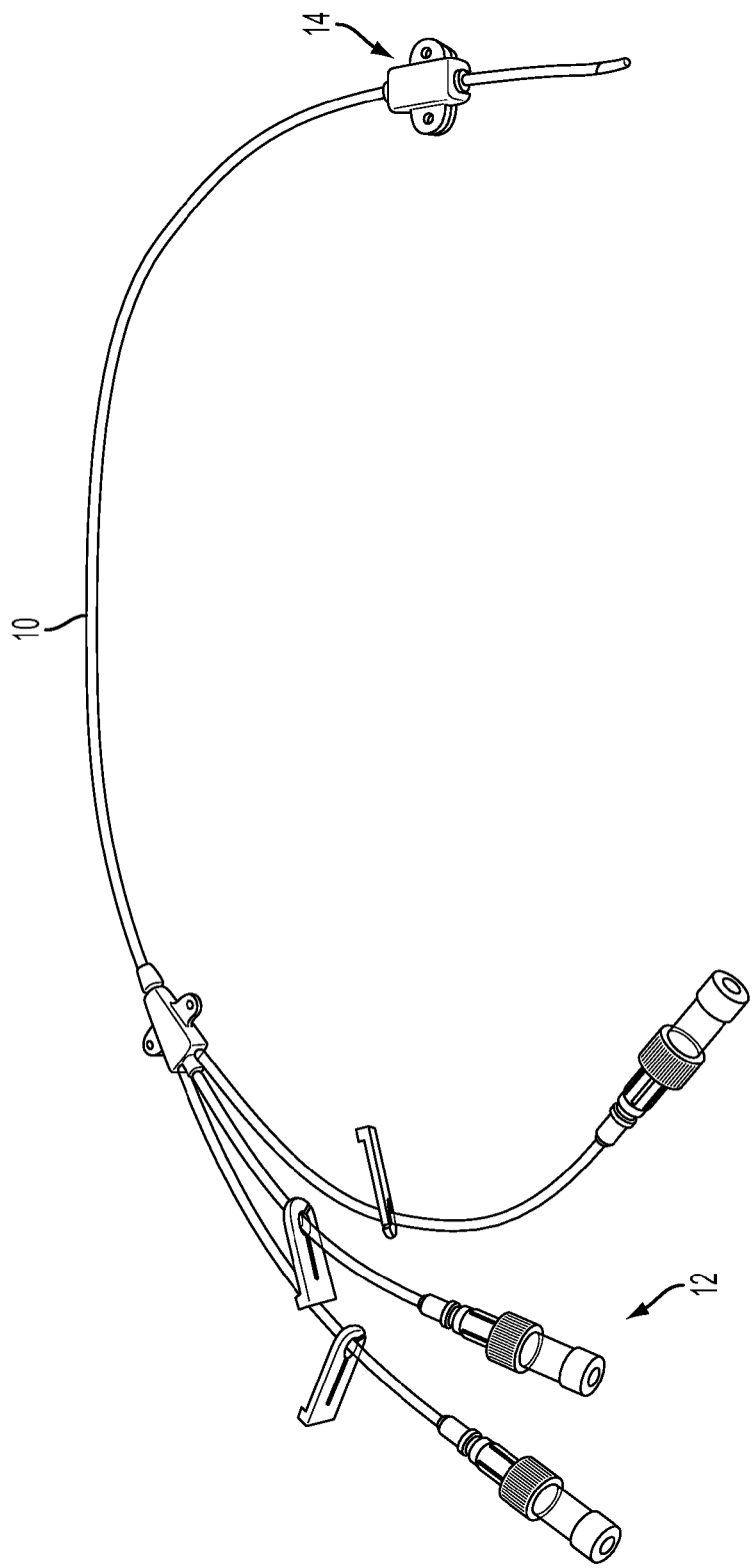
FIG. 1 is a three-dimensional view of a central venous catheter with a conventional catheter clamp system attached thereto.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
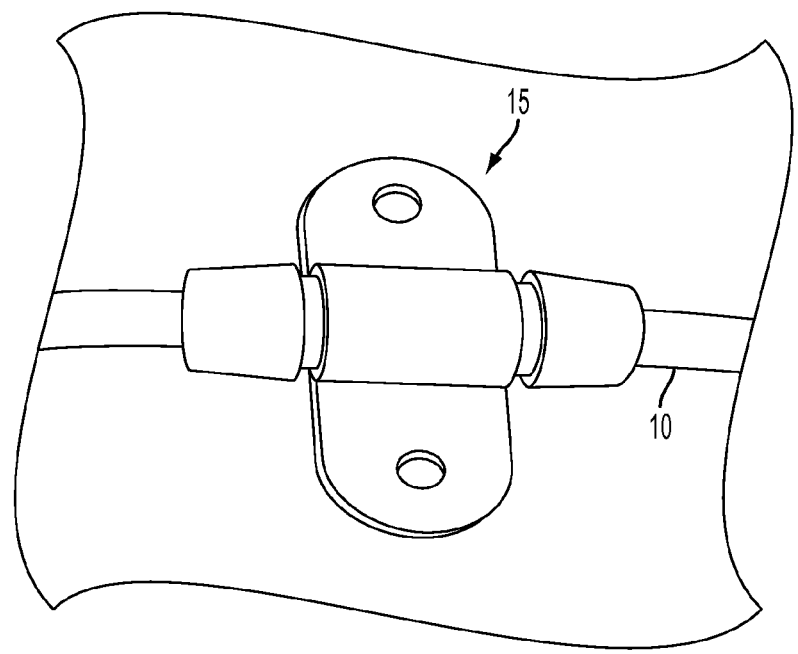
FIG. 2 is a three-dimensional view showing a silicone sleeve of the conventional catheter clamp system shown in FIG. 1.
Figure 3:
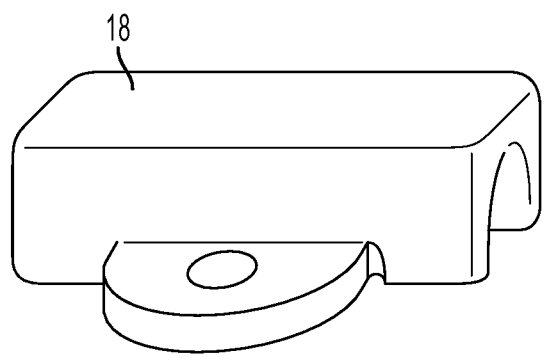
FIG. 3 is a three-dimensional view showing a clamp of the conventional catheter clamp system shown in FIG. 1.
Figure 4:
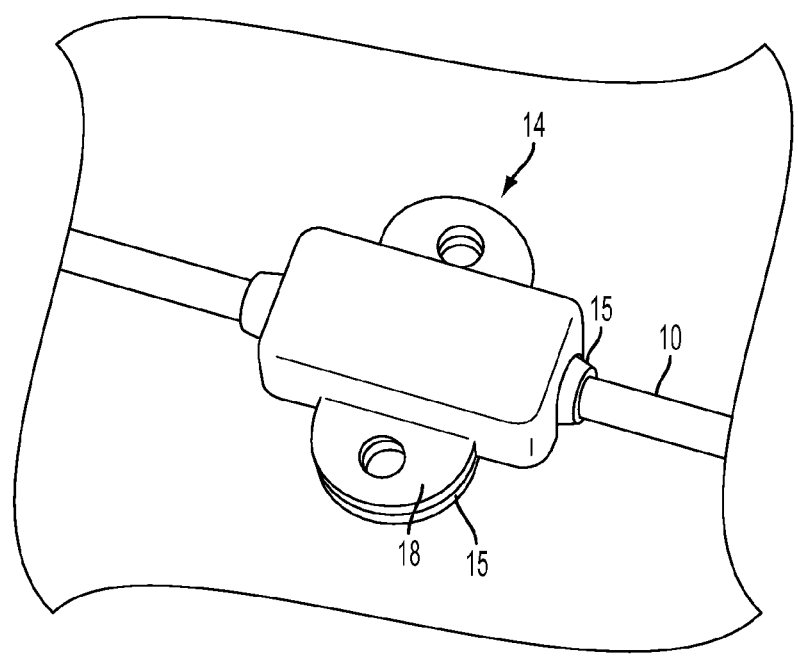
FIG. 4 is a three-dimensional view showing an enlarged view of the conventional catheter clamp system of FIG. 1.

FIG. 1 shows an example of a typical central venous catheter 10 having a large bore which is coupled to a three-port catheter system 12. Conventional catheter clamp system 14 is used to secure catheter 10 in place on the skin of a patient. Conventional catheter clamp system 14, FIG. 4, includes sleeve 15, FIG. 2, which is inserted over catheter 10 and clamp 18, FIG. 3, which is secured (snapped) to sleeve 15. FIG. 4 shows an example of a conventional catheter clamp system 14, comprising sleeve 15, FIG. 2, in place over catheter 10 and clamp 18, FIG. 3, secured to sleeve 15.

Conventional catheter clamp system 14, FIGS. 1 and 4, is then stitched to the skin of a patient to hold it in place. However, stitching catheter clamp system 14 to the skin of a patient takes time and is more prone to accidental needle stick injuries to the medical professional and/or transmission of infection from the patient to the medical professional as a result of such needle stick injuries.

Figure 5:
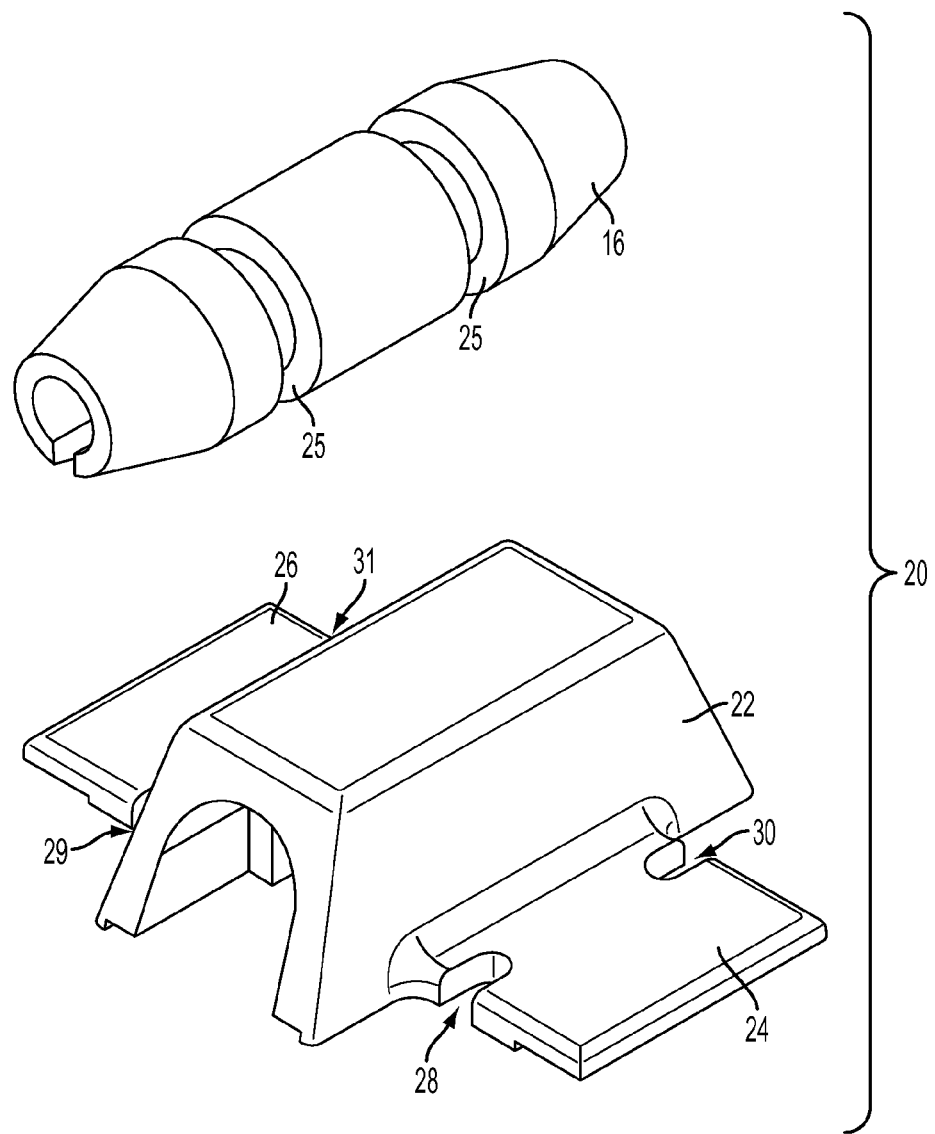
FIG. 5 is a three-dimensional view of one embodiment of the medical clamp fastener system of this invention.
Figure 6:
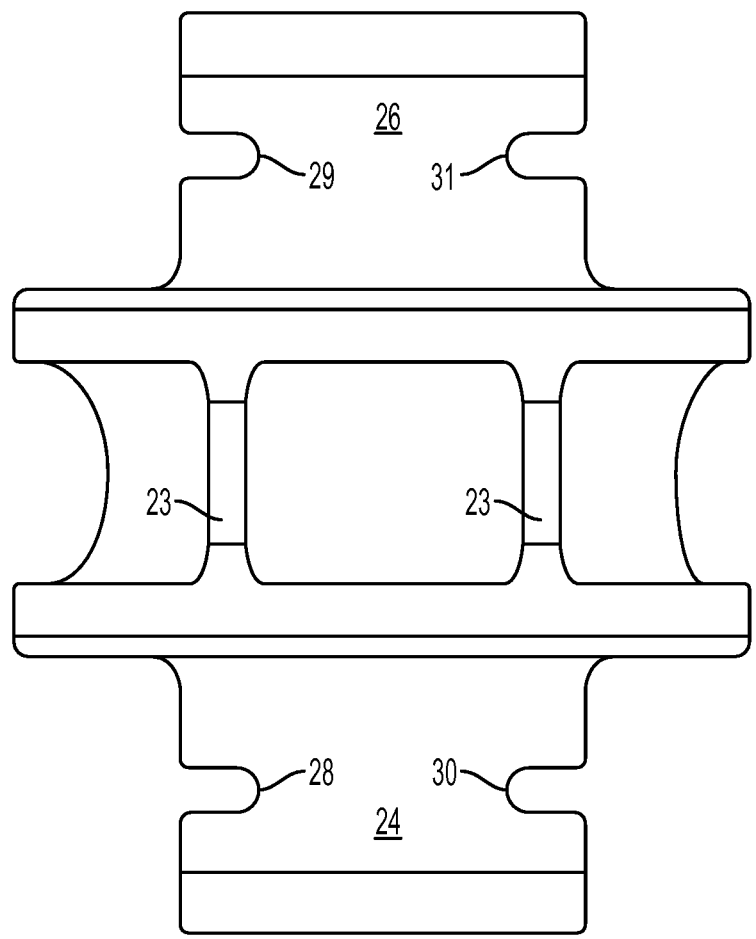
FIG. 6 is a three-dimensional bottom view of the medical clamp shown in FIG. 5.
Figure 7:
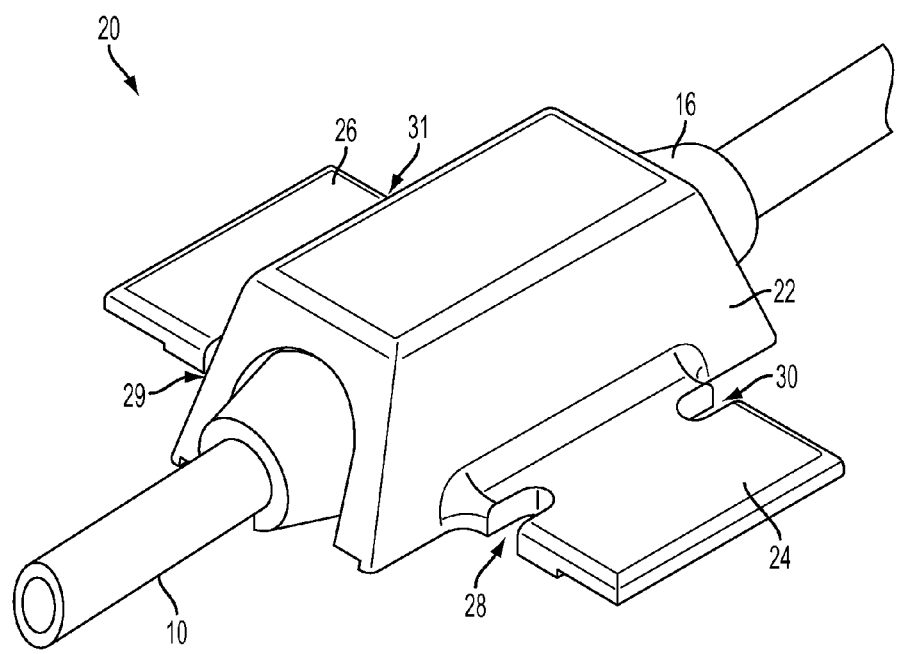
FIG. 7 is a three-dimensional view showing one example of the medical clamp shown in FIGS. 5 and 6 secured to a sleeve coupled to a catheter.

In contrast, medical clamp fastener system 20, FIG. 5, of one or more embodiments of this invention includes a sleeve 16 which is placed over catheter 10, FIG. 7, similar as discussed above with reference to FIGS. 1-4. System 20, FIG. 5, also includes medical clamp 22 configured to be secured to sleeve 16. Clamp 22 preferably includes circular shaped notches 23, FIG. 6, which engage circular shaped grooves 25, FIG. 5, in sleeve 16 to secure clamp 22 to sleeve 16. FIG. 7 shows one example of sleeve 16 about catheter 10 and clamp 22 secured to sleeve 16.

Figure 8:
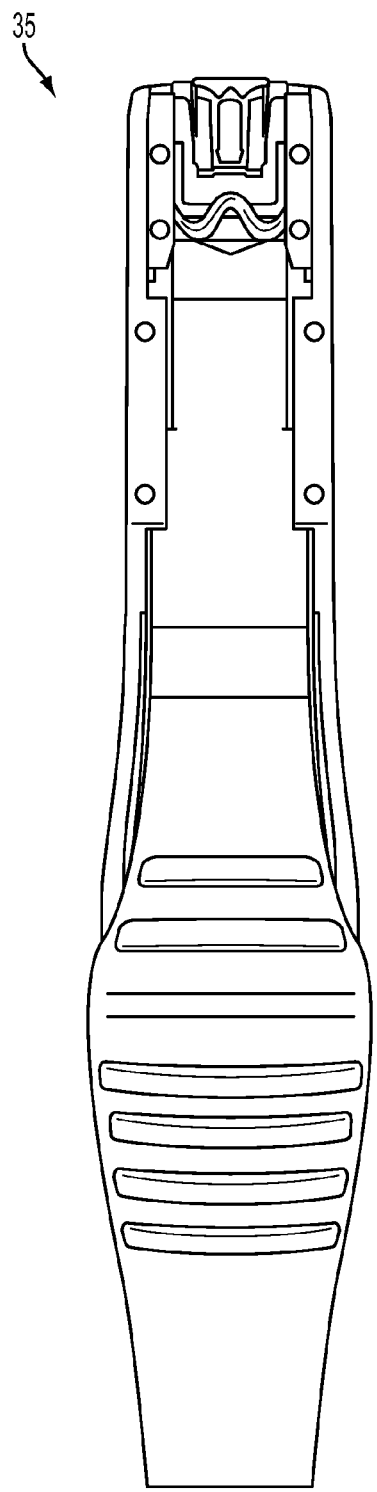
FIG. 8 is a three-dimensional view of a conventional surgical stapler which may be used to secure the medical clamp shown in FIGS. 5-7 to the skin of a patient.

Medical clamp 22, FIG. 5, includes flanges 24 and 26 which each include notches, e.g., notches 28, 30 on flange 24, and notches 29, 31 (shown in further detail in FIG. 6) on flange 26, each of which are configured to receive a surgical staple therein. The notches on the flanges allow the surgical staples to extend into the skin of the patient to secure clamp 22 to the skin of a patient. In one example, conventional surgical stapler 35, FIG. 8, may be used to staple medical clamp 22, FIG. 7, to the skin of patient to secure medical clamp system 20 coupled to catheter 10.

Medical clamp system 20 or variations thereof may be used to secure catheters or other devices, such as gastric feeding tubes (or "G-tubes"), jejunostomy tubes ("J-tubes"), or wires, to a patient's skin. The portion of such devices affixed to the patient's skin may have a generally tube-shaped configuration.

One exemplary device that may be used with medical clamp system 20 is a temporary transvenous pacemaker. In particular, the wire of a temporary transvenous pacemaker may be affixed to the skin of a patient using medical clamp system 20 or a variation thereof. The wire of the temporary transvenous pacemaker may have a diameter that is approximately one-fifth the diameter of a central venous catheter. To compensate for such differences, sleeves having different inner diameters may be used with medical clamp system 20.

Figure 9:
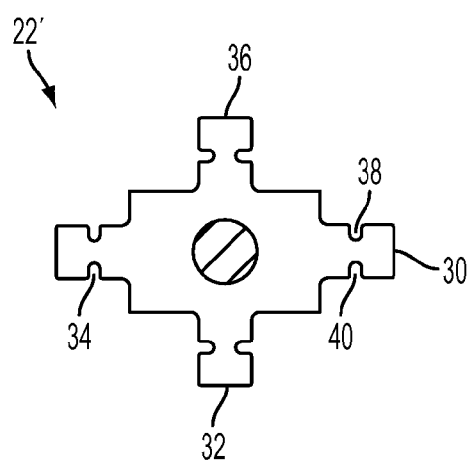
FIG. 9 is a three-dimensional view of another embodiment of the medical clamp fastener system of this invention used to secure a G-tube or J-tube in place on a patient.
Figure 10:
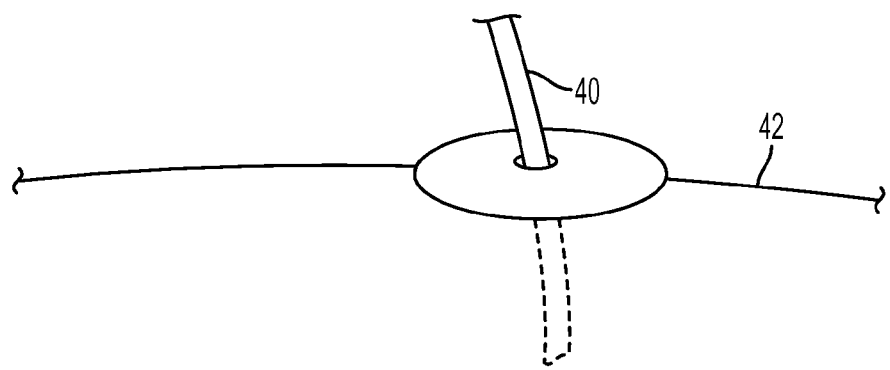
FIG. 10 is a three-dimensional view showing an example of a G-tube or J-tube in place in the abdomen of a patient.

G-tubes and J-tubes may have diameters about ten times greater than catheter tube 10, FIG. 7. FIG. 10 shows an example of G-tube 40 inserted through abdomen 42 of a patient. Clamp 22', FIG. 9, in this example, preferably includes a plurality of flanges 30, 32, 34, 36, which each similarly include notches, e.g., notches 38 and 40 on flange 30, designed to receive a surgical staple and secure medical clamp 22' to the skin of a patient to ensure the G-tube or J-tube stays in place on a patient.

The medical clamp system 20 described herein may save time by using surgical staples that can be quickly and easily used to secure medical clamp 22 to the skin of a patient. Because system 20 uses surgical staples, system 20 provides a more secure attachment to the skin of a patient than conventional catheter clamp systems. Using staples is also less prone to accidental needle stick injuries to the medical professional and/or transmission of infection from the patient to the medical professional as a result of such needle stick injuries.

Although as discussed above, a conventional surgical stapler may be used to secure medical clamp system 20 to a patient, there may be problems associated with using a conventional surgical stapler. For example, using a conventional surgical stapler may be cumbersome and difficult to use with medical clamp 22 because it may require the use of both right and left hands. Moreover, aligning the anvil with the notches of one or more embodiments of the medical clamp may be difficult. Another problem associated with using a conventional surgical stapler may be that the thickness of flanges 24, 26, FIGS. 5-7 of medical clamp 22 and/or flanges 30-36 of clamp 22', FIG. 9, may be too thick for the surgical staples used with a conventional surgical stapler. As a result, the staples may not extend at a sufficient depth to effectively secure medical clamp 22 to the skin of a patient.

Figure 11:
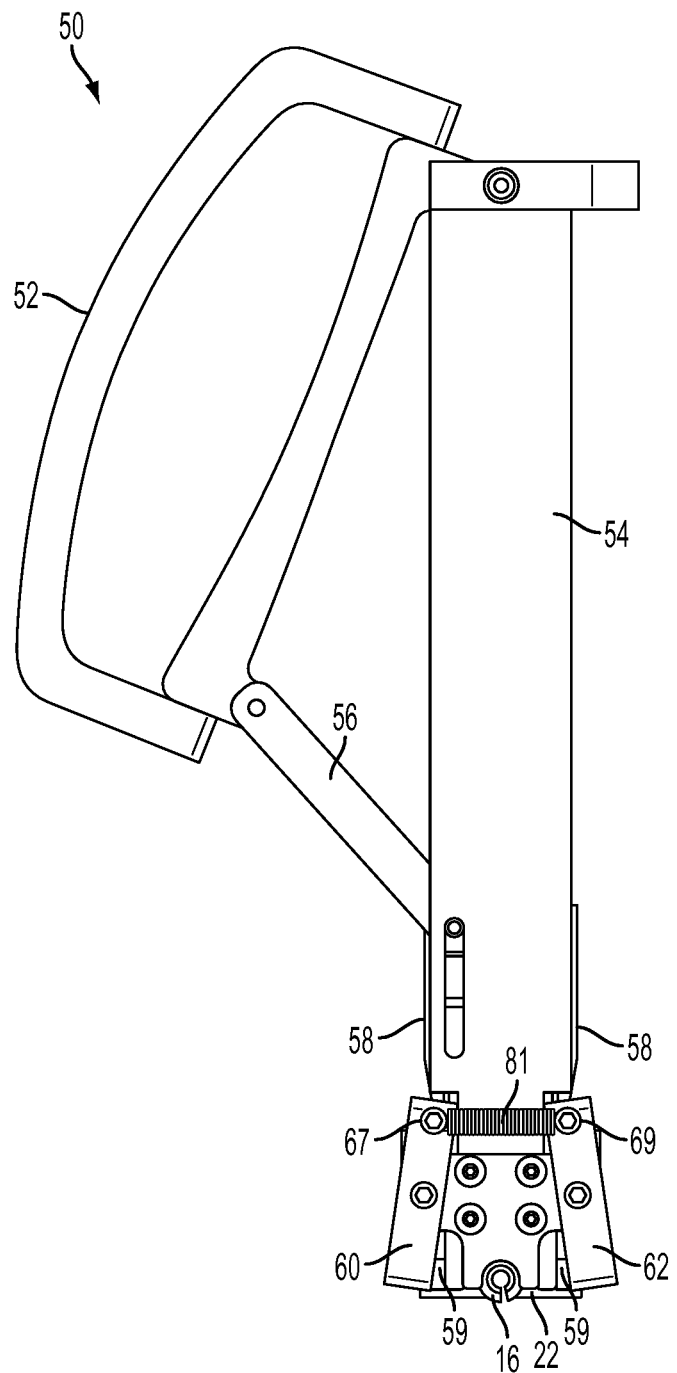
FIG. 11 is a schematic front view of one embodiment of the surgical stapler of this invention used to secure a medical clamp to a patient, such as the medical clamp shown in FIGS. 5-7 and 9.
Figure 12A:
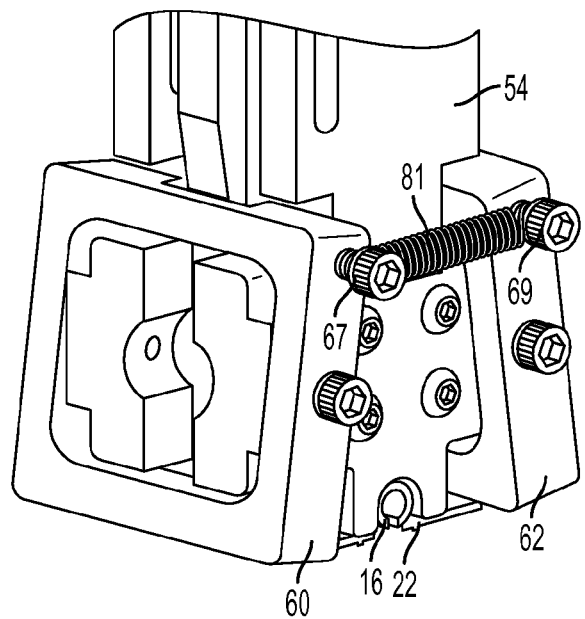
FIG. 12A is a perspective view showing in further detail the structure of the anvil members and the plunger shown in FIG. 11.
Figure 12B:
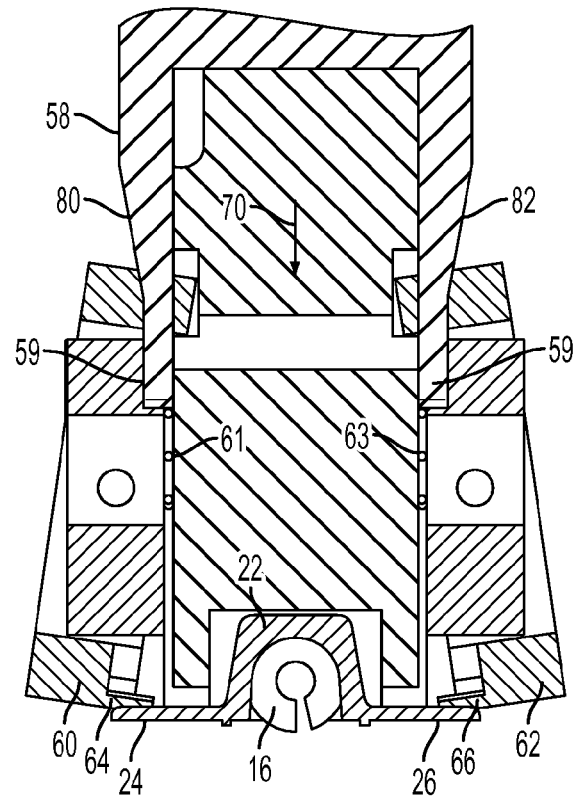
FIG. 12B is a cross-sectional view of the portion of the surgical stapler shown in FIG. 12A.
Figure 13:
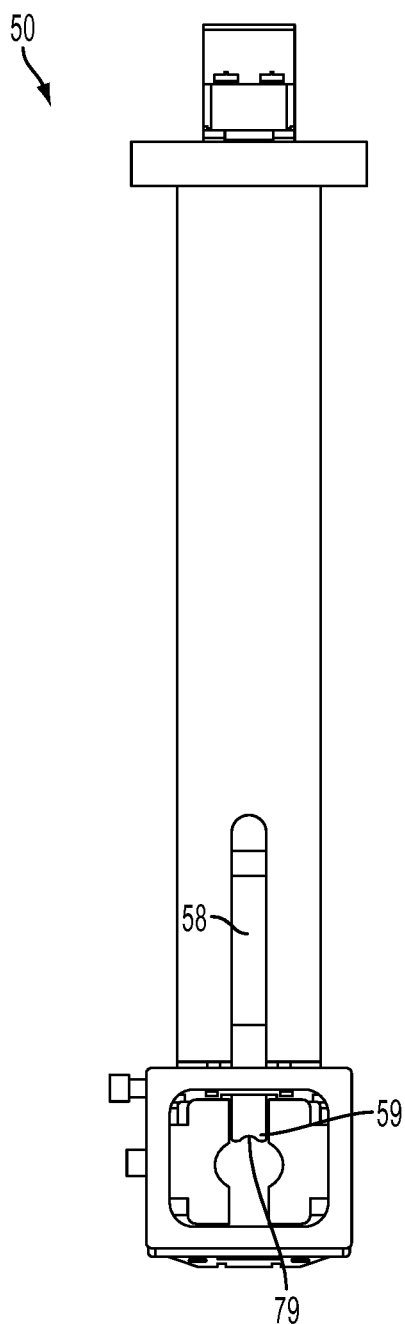
FIG. 13 is a schematic side view of the surgical stapler shown in FIG. 11.
Figure 14:
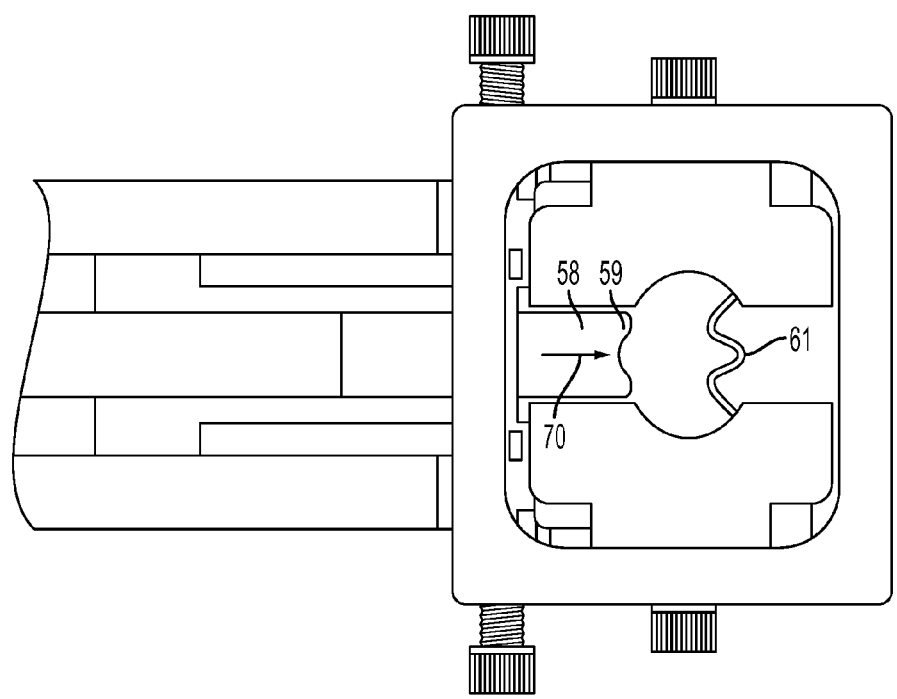
FIG. 14 is an enlarged view showing one example of a surgical staple in place below the plunger shown in FIG. 13.

To overcome these problems, surgical stapler 50, FIG. 11 of one embodiment of this invention is designed to be used with medical clamp 22, FIGS. 5-7 and 9, or similar type medical clamps. Surgical stapler 50, FIG. 11, includes handle 52 pivotably attached to base 54. Linking member 56 is attached to handle 52 on one end and to moveable plunger 58 on the other end. Plunger 58 is preferably symmetrical on both sides, as shown in further detail in FIG. 12B, and includes ends 59 which each engage a staple, e.g., staples 61, 63. Ends 59 preferably have a rounded shape, e.g., as shown at 79, FIG. 13, which is designed to engage the top of staples 61, 63, FIG. 12B, as they are stapled to the skin of a patient. FIG. 14 shows an enlarged top view of one side of plunger 58 with end 59 which, in this example, engages staple 61.

Figure 15:
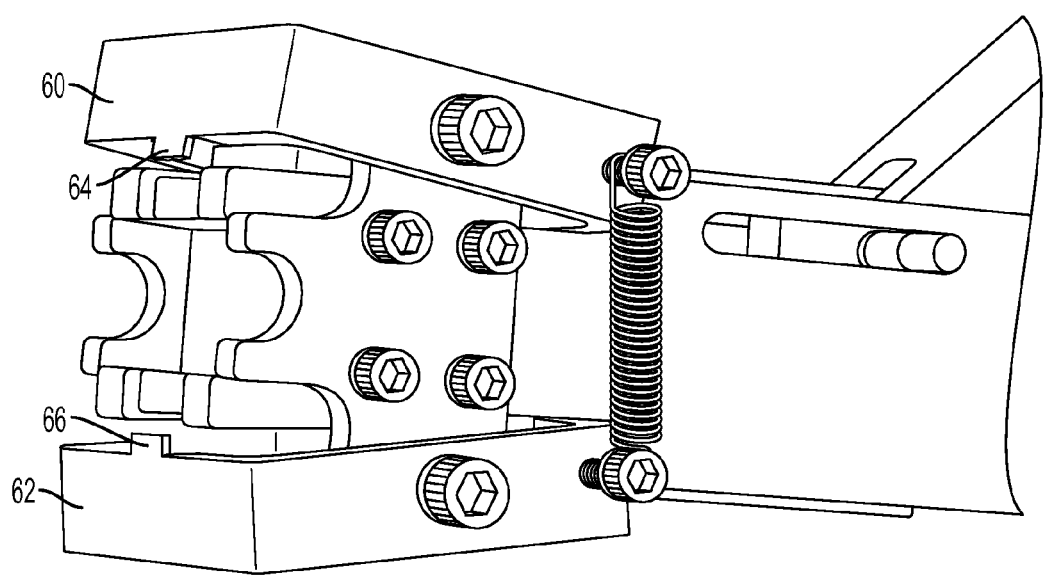
FIG. 15 is a three-dimensional view showing in further detail one example of the shape of the anvils shown in FIG. 12B.

Surgical stapler 50, FIG. 11, includes two opposing anvil members 60 and 62 pivotably coupled to base 54, e.g., with screws 67, 69. In one design, springs, e.g., spring 81, FIG. 12A, may be used to maintain anvil members 60, 62, in the open position as shown in FIG. 11. Anvil members 60, 62, FIGS. 12A and 12B, each include anvils 64, 66, respectively. Anvils 64, 66 are shaped to bend staples 61, 63, respectively, above flanges 24, 26, FIGS. 5-7, of clamp 22 and into the skin of a patient. FIG. 15 shows an enlarged view of anvil members 60 and 62 and anvils 64 and 66.

Figure 16:
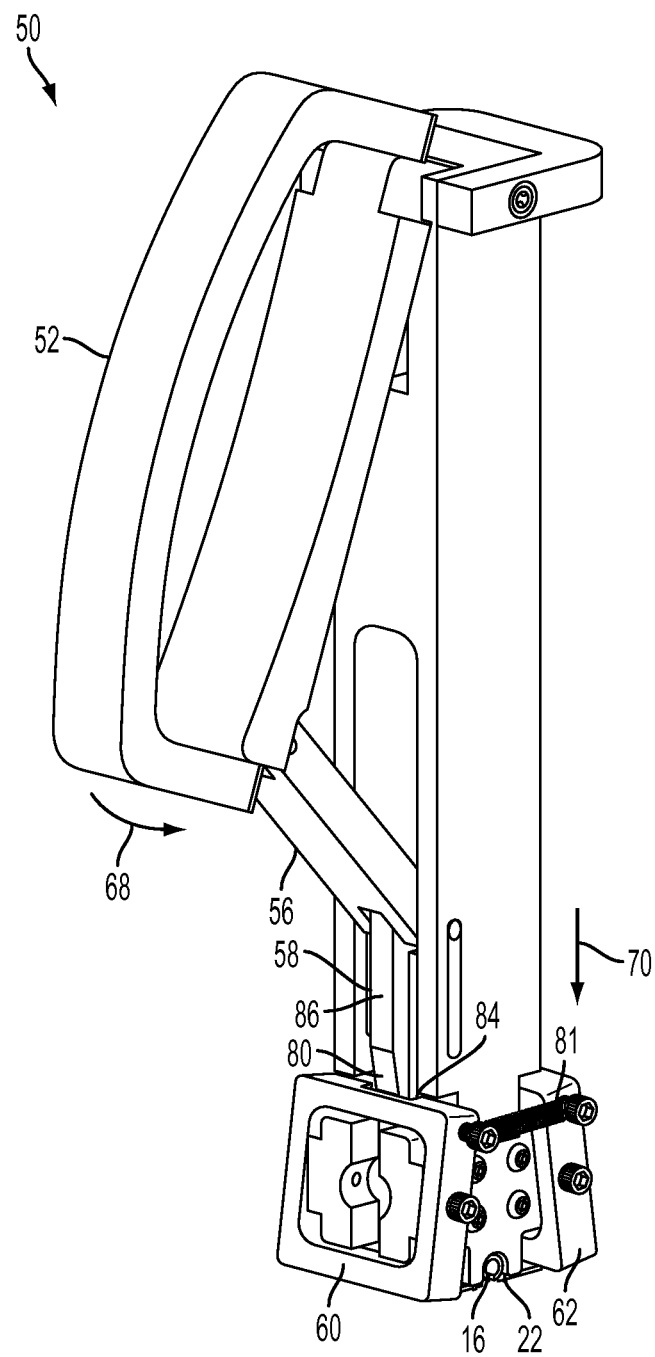
FIGS. 16 and 17 are three-dimensional views showing one example of the operation of the surgical stapler shown in FIGS. 11-15.
Figure 17:
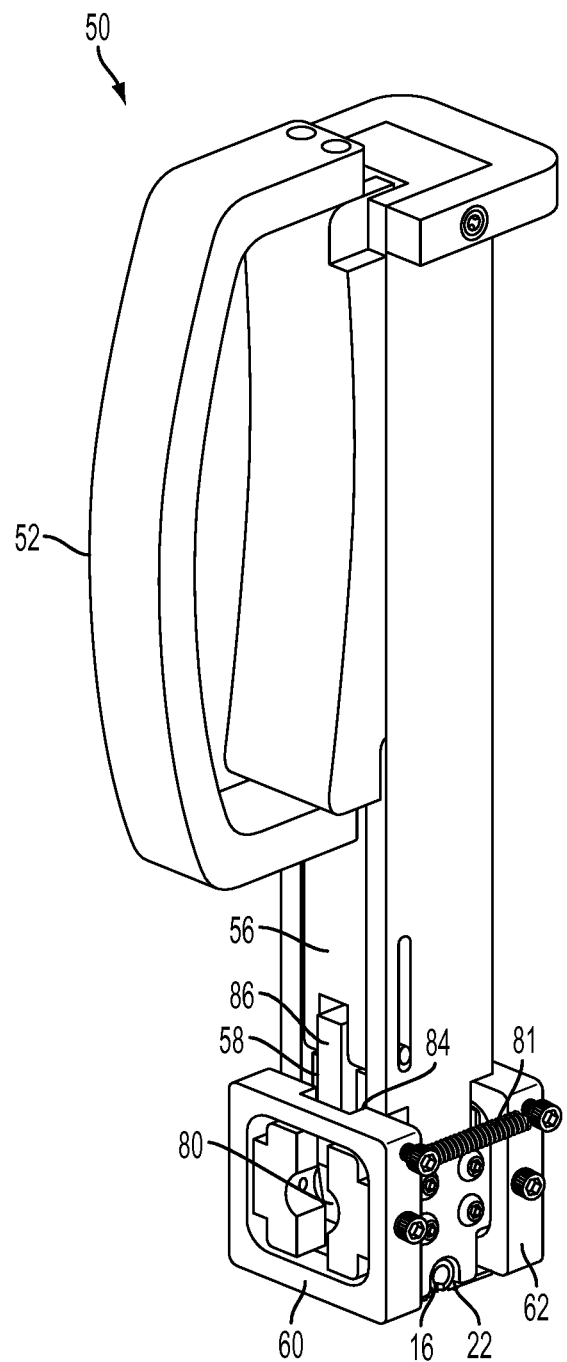

Anvil members 60 and 62, FIG. 11, are spread out, or in the open position, as discussed above, when handle 52 is not depressed. Plunger 58, FIG. 12B, preferably includes opposing sloped shoulders 80, 82 which engage anvil members 60, 62, respectively, when plunger 58 is moved downward. For example, when handle 52, FIG. 16, is pressed downward, as shown by arrow 68, plunger 58 moves in the downward direction, as shown by arrow 70. This causes shoulders 80, 82, FIG. 12B, to pass through the notches in anvil members 60, 62 and move them to the closed position as shown in FIG. 17. For example, shoulder 80, FIG. 16, passes through notch 84 and area 86 of plunger 58 causes anvil member 60 to move to the closed position, as shown in FIG. 17. At this point, plunger 58 has pushed staples 61 and 63, FIG. 12B into the notches of medical clamp 22, FIG. 5-7, while anvils 64 and 66, FIG. 12B, bend staples 61 and 63 above the flanges of medical clamp 22 to secure medical clamp 22 to the skin of a patient.

Although as discussed above with reference to FIGS. 11-17, surgical stapler is shown to staple two staples in the notches on the opposing flanges of medical clamp 22 as shown in FIGS. 5-7, this is not a necessary limitation of this invention. In other examples, stapler 50 may be designed to deliver one staple for use with a medical clamp, such as medical clamp 22', FIG. 9, e.g., for gastric G-tubes, J-tubes, and the like.

Stapler 50 may align the surgical staples with the notches of medical clamp 22 and insert them at a sufficient depth so that medical clamp 22 is properly secured to the skin of a patient. Stapler 50 is easy to use with medical clamp 22 and can be used with one hand.

Figure 18A:
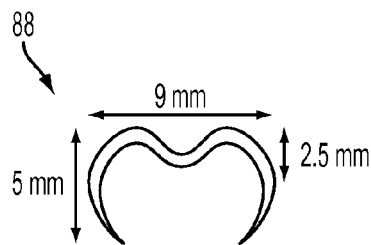
FIG. 18A is a side view of a conventional staple in an undeployed state.
Figure 18B:
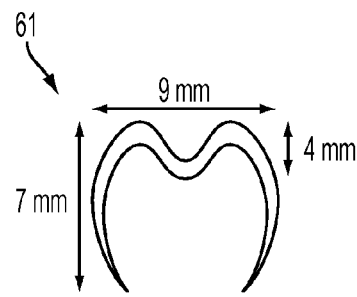
FIG. 18B is a side view of the staple of FIG. 14 in an undeployed state.
Figure 18C:
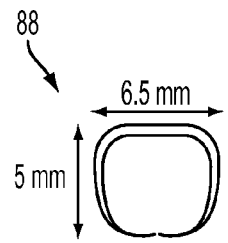
FIG. 18C is a side view of the staple of FIG. 18A in a deployed state.
Figure 18D:
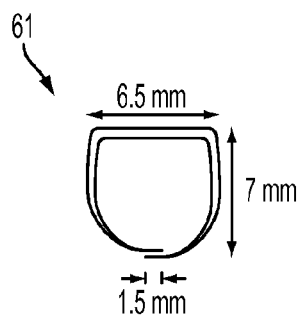
FIG. 18D is a side view of the staple of FIG. 18B in a deployed state.

FIGS. 18A-D show a conventional staple 88 contrasted with an exemplary staple 61 that may be used with the stapler 50 and medical clamps 22 and 22' described herein. As shown in FIG. 18A, the conventional staple 88 has a width of 9 mm and a height of 5 mm prior to deployment. The top of staple 88 includes two rounded bumps having a height of 2.5 mm, as measured from the base of the bumps to the top of the bumps. In contrast, staple 61, shown in FIG. 18B, has a greater height, which allows deeper penetration of the staple into the skin. In particular, staple 61 has a width of approximately 9 mm and a height of approximately 7 mm prior to deployment. The top of staple 61 includes two rounded bumps having a height of approximately 4 mm, as measured from the base of the bumps to the top of the bumps. FIG. 18C shows the conventional staple 88 after deployment. The staple 88 is deployed by applying a downward force to the bumps, thereby flattening them. The ends of the deployed staple 88 are pushed together, but do not overlap. The deployed staple 88 has a width of 6.5 mm and a height of 5 mm. FIG. 18D shows the staple 61 after deployment. Similar to staple 88, staple 61 is deployed by applying a downward force to the bumps, thereby flattening them. The ends of the deployed staple 61 are pushed together and overlap in parallel fashion by approximately 1.5 mm. The deployed staple 61 has a width of approximately 6.5 mm and a height of approximately 7 mm. Staple 61 may be formed of surgical stainless steel or another suitable material.

Staple 61, which may be the same as staple 63 described herein, differs from staple 88 in at least two ways. First, the height of the staple 61 is greater, which allows for deeper penetration of the staple into the skin. The height of staple 61 may be such that the staple penetrates tissue by an optimal holding depth without risking damages to the structures underlying the skin, such as blood vessels and nerves. Second, in the deployed state, the staple 61 includes overlapped ends, which form a "virtual" closed circle. Thus, the deployed staple 61 may be more stable in the skin than staple 88, which does not have overlapping ends in the deployed state.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A fastening device for actuating first and second fasteners to secure a medical clamp to a patient, the fastening device comprising:
    a plunger having a first shoulder, a second shoulder, a first end configured to engage the first fastener, and a second end configured to engage the second fastener, wherein the plunger is configured to move in a downward direction towards the first end and the second end;
    a first rotatable member configured to rotate about a first pivot axis from an outward position to an inward position by the first shoulder contacting an inner surface of the first rotatable member as the plunger moves in the downward direction to engage the first fastener, wherein the first rotatable member is pivotably coupled to a base at the first pivot axis;
    a second rotatable member configured to rotate about a second pivot axis from an outward position to an inward position by the second shoulder contacting an inner surface of the second rotatable member as the plunger moves in the downward direction to engage the second fastener, wherein the second rotatable member is pivotably coupled to the base at the second pivot axis; and
    a member positioned between the first rotatable member and the second rotatable member, wherein the first end is configured to move between the member and the first rotatable member and the second end is configured to move between the member and the second rotatable member as the plunger moves in the downward direction;
    a first anvil positioned on the inner surface of the first rotatable member and configured to move inwardly; and
    a second anvil positioned on the inner surface of the second rotatable member and configured to move inwardly, and
    wherein the first and second rotatable members are mechanically coupled to enable concurrent engagement of the first and second fasteners.

2. The fastening device of claim 1, further comprising a mechanical interface configured to align the fastening device with the medical clamp.

3. The fastening device of claim 2, wherein the mechanical interface comprises a recess configured to receive a body portion of the medical clamp.

4. The fastening device of claim 3, wherein the recess is located between the first and second rotatable members.

5. The fastening device of claim 4, wherein:
    the first and second pivot axes are parallel to a central longitudinal axis of the recess.

6. The fastening device of claim 1, wherein the first and second rotatable members are configured to rotate toward each other from their respective outward positions to their respective inward positions.

7. The fastening device of claim 1,
    wherein the plunger is coupled to the base and is configured to apply a downward force to the first and second fasteners.

8. The fastening device of claim 7, further comprising:
    a handle, coupled to the base via at least one pivot, wherein rotation of the handle about an axis corresponding to the at least one pivot causes the plunger to move in the downward direction.

9. The fastening device of claim 1, wherein the first and second rotatable members are configured to bend the first and second fasteners, respectively.

10. The fastening device of claim 1, further comprising:
    a spring coupled to both the first rotatable member and the second rotatable member, wherein the spring is configured to maintain the first rotatable member and the second rotatable member in their respective outward positions.

11. The fastening device of claim 1, wherein the first anvil and the second anvil rotate towards the member as the plunger moves in the downward direction.

12. The fastening device of claim 11, wherein the first anvil is more proximate to the first end of the plunger when the first rotatable member is at the inward position than at the outward position, and wherein the second anvil is more proximate to the second end of the plunger when the second rotatable member is at the inward position than at the outward position.

* * * * *